(12) United States Patent
Rudling et al.

(10) Patent No.: US 6,559,289 B1
(45) Date of Patent: May 6, 2003

(54) USE OF GROWTH HORMONE OR ANALOGUES THEREOF FOR THE TREATMENT OF MAMMALS WITH FAMILIAL HYPERCHOLESTEROLEMIA

(75) Inventors: Mats Rudling, Sollentuna (SE); Bo Angelin, Stockholm (SE)

(73) Assignee: Salhtech I Goteborg AB (SE)

( * ) Notice: Subject to any disclaimer, the term of this patent is extended or adjusted under 35 U.S.C. 154(b) by 0 days.

(21) Appl. No.: 09/830,077

(22) PCT Filed: Oct. 21, 1999

(86) PCT No.: PCT/SE99/01898

§ 371 (c)(1),
(2), (4) Date: Apr. 23, 2001

(87) PCT Pub. No.: WO00/23097

PCT Pub. Date: Apr. 27, 2000

(30) Foreign Application Priority Data

Oct. 22, 1998 (SE) .............................................. 9803623

(51) Int. Cl.[7] .......................... A61K 38/27; A61K 38/00
(52) U.S. Cl. .......................... 530/399; 530/324; 514/2; 514/12; 514/805; 930/120; 435/69.4
(58) Field of Search .............................. 514/12, 2, 805; 530/399, 324; 930/120; 435/69.4

(56) References Cited

PUBLICATIONS

M. Rudling et al., "Effects of Growth Hormone on Hepatic Cholesterol Metabolism. Lessons From Studies in Rats and Humans", Growth Hormone & IGF Research, vol. 9, No. 1–7, pp. 1–7 (1999).
Bo Angelin, "Therapy for Lowering Lipoprotein (a) Levels", Current Opinion in Lipidology, vol. 8, pp. 337–341 (1977).
Serena Tonstad et al, "The Effect of Growth Hormone on Low–Density Lipoprotein Cholesterol and Lipoprotein (a) Levels in Familial Hypercholesterolemia", vol. 45, No. 11, pp. 1415–1421 (1996).
M. Rudling et al, "Effects of Growth Hormone on Hepatic Cholesterol Metabolism", Growth Hormone & IGF Research, 1999, pp. 1–7, vol. 9, No. 1–7.
Bo Angelin, "Therapy for Lowering Lipoprotein (a) Levels", Current Opinion in Lipidology, 1997, vol. 8, pp. 337–341.
Serena Tonstad et al, "The Effect of Growth Hormone on Low–Density Lipoprotein Cholesterol and Lipoprotein(a) Levels in Familial Hypercholesterolemia", Metabolism, 1996, vol. 45, No. 11, pp. 1415–1421.
Joseph L. Goldstein et al, "Familial Hypercholesterolemia", Lipoprotein and Lipid Metabolism Disorders, 1995, Chapter 62, pp. 1981–2030, ed. by C.R. Scriver et al. New York: McGraw–Hill, 1995.
Shun Ishibashi et al, "Hypercholsterolemia in Low Density Lipoprotein Receptor Knockout Mice and its Reversal by Adenovirus–mediated Gene Delivery", J. Clinical Invest., Aug. 1993, vol. 92, pp. 883–893.

Guorong Xu et al, "Unexpected Inhibition of Cholesterol 7α–Hydroxylase by Cholesterol in New Zealand White and Watanabe Heritable Hyperlipidemic Rabbits", The Journal of Clinical Investigation, Inc., Apr. 1995, vol. 95, pp. 1497–1504.
David K. Spady et al, "Adenovirus–mediated Transfer of a Gene Encoding Cholesterol 7α–Hydroxylase into Hamsters Increases Hepatic Enzyme Activity and Reduces Plasma Total and Low Density Lipoprotein Cholesterol", J. Clin. Invest., Aug. 1995, vol. 96, pp. 700–709.
A David Marais et al, "Decreased Production of Low Density Lipoprotein by Atorvastatin After Apheresis in Homozygous Familial Hypercholesterolemia", Journal of Lipid Research, 1997, vol. 38, pp. 2071–2078.
Mats Rudling et al, "Importance of Growth Hormone for the Induction of Hepatic Low Density Lipoprotein Receptors", Proc. Natl. Acad. Sci. USA, Aug. 1992, vol. 89, pp. 6983–6987.
Mats Rudling et al, "Growth Hormone and Bile Acid Synthesis" J. Clin. Invest., May 1997, vol. 99, No. 9, pp. 2239–2245.
Paolo Parini et al, "Cholesterol and Lipoprotein Metabolism in Aging" Arterioscler Thromb Vasc Biol, Apr. 1999, vol. 19, pp. 832–839.
Bo Angelin, "Therapy for Lowering Lipoprotein (a) Levels", Current Opinion in Lipidology, 1997, vol. 8, pp. 337–341.
Mats Rudling, "Hepatic mRNA levels for the LDL Receptor and HMG–CoA Reductase Show Coordinate Regulation in vivo", Journal of Lipid Research, 1992, vol. 33, pp. 493–502.
Bo Angelin et al, "3–Hydroxy–3–Methylglutaryl Coenzyme A Reductase in Human Liver Microsomes: Active and Inactive Forms and Cross–Reactivity with Antibody Against Rat Liver Enzyme", The Journal of Lipid Research, 1984, vol. 25, No. 11, pp. 1159–1166.
Serena Tonstad et al, "The Effect of Growth Hormone on Low–Density Lipoprotein Cholesterol and Lipoprotein (a) Levels in Familial Hypercholesterolemia" Metabolism, 1996, vol. 45, No. 11, pp. 1415–1421.
Kurt Einarsson et al, "Bile Acid Synthesis in Man: Assay of Hepatic Microsomal Cholesterol 7α–Hydroxylase Activity by Isotope Dilution–Mass Spectrometry", Journal of Lipid Research, 1986, vol. 27, pp. 82–88.
Kurt Einarsson et al, "Studies on Acyl–Coenzyme A: Cholesterol Acyltransferase Activity in Human Liver Microsomes", Journal of Lipid Research, 1989, vol. 30, pp. 739–746.
Sabine Wolle et al, "Hepatic Overexpression of Bovine Scavenger Receptor Type I in Transgenic Mice Prevents Diet–Induced Hyperbetalipoproteinemia", J. Clin. Invest., Jul. 1995, vol. 96, pp. 260–272.
William T. Beher et al, "Rapid Analysis of Human Fecal Bile Acids", Steroids, Sep., 1981, vol. 38, No. 3, pp. 281–294.

Primary Examiner—Karen Cochrane Carlson
Assistant Examiner—Chih-Min Kam
(74) Attorney, Agent, or Firm—Burns, Doane, Swecker & Swecker & Mathis, L.L.P.

(57) ABSTRACT

The invention relates to the use of compounds selected from GH, analogues thereof, and GH-releasing compounds, optionally in combination with lipid-lowering agents or therapy, for the preparation of a drug for treatment of mammals with familial hypercholesterolemia of homozygous form.

8 Claims, 4 Drawing Sheets

USE OF GROWTH HORMONE OR ANALOGUES THEREOF FOR THE TREATMENT OF MAMMALS WITH FAMILIAL HYPERCHOLESTEROLEMIA

This application is a 371 of PCT/SE99/01898 filed Oct. 21, 1999, which claims the benefits of foreign priority from Sweden Application No. 9803623-9 filed Oct. 22, 1998.

BRIEF DESCRIPTION OF THE INVENTION

The present invention relates to the use of biologically active compounds selected from GH, analogues thereof and GH-releasing compounds, as lipid lowering agents for the preparation of a drug for the treatment of mammals with homozygous familial hypercholesterolemia. By the furnishing of a drug comprising compounds selected from GH, analogues thereof and GH-releasing compounds, optionally in combination with further lipid lowering treatment, elevated plasma cholesterol in LDLR deficient mammals with familial hypercholesterolemia of the homozygous form may be treated.

Growth hormone (GH) has pleiotropic effects on cholesterol metabolism. GH stimulates the expression of hepatic low density lipoprotein (LDL)-receptors and the activity of cholesterol 7α-hydroxylase (C7αOH), a key regulatory step in bile acid synthesis. According to the present invention it is shown that GH treatment reduces plasma cholesterol in the situation of homozygous familial hypercholesterolemia as represented by the recently developed LDL-receptor knockout mouse strain.

GH infusion into LDL-receptor knockout mice resulted in a 30–40% reduced plasma cholesterol level. In addition, the reduced enzymatic activities of cholesterol 7α-hydroxylase and HMG CoA reductase were normalized. It is concluded that GH treatment reduces the severe homozygous form of familial hypercholesterolemia in LDLR-deficient mice. Such therapy gives a beneficial effect in the heavily therapy resistant disease homozygous familial hypercholesterolemia, a disorder known to be strongly resistant to lipid-lowering treatment.

In this specification and the appended claims the following abbreviations are used: C7αOH, represents cholesterol 7α hydroxylase; HMG CoA reductase, represents 3-hydroxy-3-methyl-glutaryl coenzyme A reductase; FPLC, represents fast performance liquid chromatography; GH, represents growth hormone; HDL, represents high density lipoprotein; LDL, represents low density lipoprotein; LDLR, represents low density lipoprotein receptor; LDLRKO, represents low density lipoprotein receptor knockout; SDS-PAGE, represents sodium dodecyl sulphate-polyacrylamide gel electrophoresis; TNA, represents total nucleic acid; VLDL, represents very low density lipoprotein.

BACKGROUND OF THE INVENTION

Familial hypercholesterolemia (FH) is a common autosomal dominant inherited disease and is present in heterozygous and homozygous forms.

Heterozygous FH occurs at a frequency of approx. 1:300–500 in the general population. The subjects have type II-A lipid pattern and approximately twice the normal low-density lipoprotein (LDL) cholesterol levels. Heterozygotes have an increased risk to develop premature heart disease and their expected life span is reduced 10 to 15 years. FH heterozygotes have a mutation in the gene encoding the LDL receptor. This receptor is located on the surface of cells in the liver and other organs. The LDL receptors bind LDL and facilitate its uptake by receptor-mediated endocytosis and subsequent delivery to lysosomes, where the LDL is degraded yielding free cholesterol for cellular use. When LDL receptors are deficient, the rate of removal of LDL from plasma declines, and the level of LDL rises in inverse proportions to the receptor number. The excess plasma LDL is deposited in scavenger cells and other cell types, producing atheromas and xanthomas. FH heterozygotes have one normal and one mutant allele at the LDL receptor locus; hence their cells are able to bind and degrade LDL at approximately half the normal rate. (See In: The metabolic and molecular bases of inherited disease. Seventh edition, Mac Graw-Hill, Chapter 62, Familial Hypercholesterolemia, by J. L. Goldstein et al., pp 1981–2030).

Subjects with the homozygous form of FH (incidence= $1:10^6$) have plasma cholesterol levels 3–5 fold higher than normal subjects and frequently develop coronary heart disease in childhood, almost invariably before 20 years of age. Homozygotes possess two mutant alleles at the LDL receptor locus, and their cells show a total or near total inability to bind or take up LDL.

There are two animal models for FH that closely resemble the human disease. The first is a natural mutant strain of rabbits, Watanabe Heritable Hyperlipidemic (WHHL) rabbits, and the second is the recently available mouse LDLR knock-out (LDLRKO) strain developed by Herz et al (Ishibashi, S. et al. 1993. J. Clin. Invest. 92; 883–893). Previous studies in WHHL-rabbits have shown that homozygous animals have strongly suppressed activity of the regulatory enzyme C7αOH (Xu et al. 1995. J. Clin. Invest. 95; 1447–1504).

In the therapy of type II-A hyperlipidemia, the strategy is based on the concept of increasing the number of available hepatic LDL-receptors which in turn will reduce plasma cholesterol due to an increased hepatic uptake of LDL and LDL precursor lipoproteins, such as intermediate density lipoprotein, (IDL). In heterozygous FH, the most effective therapy is by interfering with the enterohepatic circulation of bile acids by orally administered bile acid sequestrants such as cholestyramine in combination with specific 3-hydroxy-3-methyl-glutaryl coenzyme A (HMG CoA) reductase inhibitors. An increasing number of such drugs (statins and vastatins) have been introduced to the market. Such combined therapy can reduce, but does seldom completely normalize plasma LDL.

However, in homozygotes that do not harbor any functional LDL receptors, other means to reduce the high LDL levels must be employed. This disease type is a candidate for gene therapy. Such treatment has been tested in laboratory animals using the LDLR gene and the gene encoding cholesterol 7α-hydroxylase (C7αOH), the key regulatory step in the synthesis of bile acids. (Ishibashi, S. et al. 1993. J. Clin. Invest. 92, 883–893, Spady, D. K. and Cuthbert, J. A. 1995. J. Clin. Invest 96; 700–709). The effects are unfortunately transient. So far, the only available therapy has been liver transplantation or plasmapheresis and/or selective extracorporeal removal of cholesterol-rich LDL-particles. The latter therapy, if performed every 2–3 weeks, can reduce but not normalize the increased plasma cholesterol level. Recently it has been shown that certain FH homozygotes can also benefit from high dose statin therapy (Marais, A. D et al. 1997. J. Lipid Res. 38:2071–8). Therefore, until gene-therapy will be clinically available, there is a need of novel pharmacological therapeutic strategies in homozygous FH.

Pituitary growth hormone (GH) has several effects on cholesterol and lipid metabolism. We have previously shown that GH therapy has a stimulatory effect on the hepatic LDLR expression in both rats and humans (Rudling, M. et al. Proc. Natl. Acad. Sci. USA. 1992, 89; 6983–6987), and in particular we have identified GH as an important stimulator of the enzymatic activity of C7αOH (Rudling et al, 1997, J. Clin. Invest. 99; 2239–2245). We have shown that GH stimulates C7αOH activity, not only in hypophysectomized animals, but also in normal young rats (P. Parini, et al. 1999, Cholesterol and lipoprotein metabolism in aging: reversal of hypercholesterolemia by growth hormone treatment in old rats, Arterioscl. Thromb. & Vasc. Biol. 19;832–839). The experiments were performed in mammals expressing normal LDL receptors.

From "Current opinion in Lipidology", 1997,Vol. 8, p. 337–341 by B. Angelin as well as from "Metabolism", 1996, Vol. 45 No. 11, p. 1414–1421 by Tostad et al. it was evident that familial hypercholesterolemia of the heterozygous form may benefit from treatment with GH because such patients express functional LDL receptors.

However, because homozygotes do not harbor functional LDL receptors, it was not for a man skilled in the art obvious that the homozygous form of the disease may benefit from GH treatment.

DESCRIPTION OF THE INVENTION

We have now surprisingly found that administration of compounds selected from GH, analogues thereof and GH-releasing compounds, optionally in combination with established lipid-lowering treatment, to mammals with familial hypercholesterolemia of homozygous form has beneficial effects on plasma cholesterol levels. We can show that the infusion of GH to LDLR deficient animals reduces total plasma and LDL cholesterol levels. This occurs in parallel with a normalization of a suppressed C7αOH enzymatic activity. In addition, we have also found that GH treatment can potentiate the effect of statins and bile acid sequestrants, two important classes of lipid lowering drugs used in established treatment of patients.

By the present invention it is also shown that GH therapy can be used to reduce plasma LDL cholesterol in FH of the homozygous form. Thus GH treatment alone, optionally in combination with established lipid lowering treatment, can be used to treat mammals characterized by a deficiency of LDL receptors. Therefore, GH could become an adjuvant to current therapy of FH-homozygotes.

DETAILED DESCRIPTION OF THE INVENTION

The present invention is directed to the use of compounds selected from GH, analogues thereof and GH-releasing compounds, optionally in combination with conventional lipid lowering agents, for the preparation of a drug which reduces the serum lipids in a mammal that displays the syndrome of FH of the homozygous form. The therapy may also be combined with established lipid-lowering treatment. The type of GH that can be used includes natural or recombinant GH, and variant molecules of GH or analogues with the common denominator of ultimately being capable to activate a GH receptor signal in cells in the species that displays the syndrome of FH of homozygous form. One example of GH is Genotropin, which is manufactured by Pharmacia & Upjohn. Examples of analogues are compounds that can enhance GH release or interfere with the cellular mechanisms of GH action. Compounds that cause GH release is exemplified by GH-releasing hormone, somatostatin-antagonists, hexarelin, and the Merck growth hormone releasing compound L-692 429. The route of GH administration to mammals can vary and a common way of administration is by injection therapy. Alternative routes of administration may however be applicable in the practice of the present invention. Such alternative routes for GH administration that presently exist or may be developed include oral, nasal, rectal and transdermal GH therapy. The dose of GH to be used for the treatment of the syndrome of FH of homozygous form may vary dependent on the GH used and the species to be treated as well as the clinical evaluation of a patient. In humans, GH would preferably be injected 7 times a week but less frequent injections could be used as long as the criteria of activating a GH receptor signal that results in reduction of cholesterol is met.

One embodiment of the present invention includes the combined treatment with GH and a lipid lowering therapy as LDL apheresis or with compounds preferably selected from the list of lipid lowering drugs that include for example statins, and bile acid sequestrants such as cholestyramine. Today there are five statins available on the market in Sweden, atorvastatin, cerivastatin, fluvastatin, pravastatin and simvastatin.

The dose ranges of these drugs will be the ones recommended by the respective suppliers for clinical use. The daily dose of human GH (such as Genotropin) would preferably be in range from 0.02 to 0.14 IU/kg depending on the responses obtained. The duration of treatment according to the present invention includes GH treatment in a continuous or in a discontinuous fashion with or without the combination of other types of lipid lowering drugs or procedures. The duration of treatment is dependent on the judgement of the responsible physician. It is preferable that the duration of treatment is lasting for several months and that the effect of treatment is monitored at least every half year by analysis of serum cholesterol.

The syndrome of FH suitable for treatment according to the present invention includes homozygous LDLR mutations of any kind that result in deficient LDLR function. Such patients can be identified clinically from an elevated plasma cholesterol value. In a more refined diagnosis the LDLR gene could be sequenced or the pattern of lipoproteins determined.

This invention includes all embodiments disclosed in the appended claims.

In the following we provide examples that illustrate the present invention. These examples only serve the purpose of illustration of the invention and are not to be considered limitations thereof.

Methods

Animals and Experimental Procedure

The studies were approved by the Institutional Animal Care and Use Committee, Sweden. Altogether 75 male LDLRKO and 45 C57 BL/6J mice were purchased from Bommice, Denmark. Animals were housed under standardized conditions in groups of ten. The mice had free access to water and chow; the light cycle hours were between 6 a.m. and 6:00 p.m. At the start of the experiment, osmotic mini pumps containing GH were implanted subcutaneously under light ether anesthesia. Non-GH treated animals were sham-operated. Recombinant human GH (Genotropin®), purchased from Pharmacia & Upjohn, was infused at a rate of 1.0 mg/kg per day. After six days of infusion, animals where anesthetized with ether, and blood was collected from the eye. The mice where thereafter killed by cervical dislocation. The livers were immediately removed and when indicated, 1 g of liver was taken for subsequent preparation of microsomes for assay of enzyme activity as described below. The remaining liver was immediately frozen in liquid nitrogen and stored at −70° C.

In the experiment comparing the effects of cholestyramine, atorvastatin, GH, and combinations thereof, animals were bled from the eye under light ether anesthesia and were not killed. Feces were collected at two occasions during two days, the first period starting 4 days prior to initiation of treatment and the second from day 3 to day 5 during drug treatment. Animals were allowed to walk on a metal grid during the two days of feces collection. Samples were collected daily and pooled. Cholestyramine (Questran™), obtained from Bristol-Myers Squibb, was added to ground mouse chow at a final concentration of 2%. Atorvastatin (Lipitor™) was purchased from Parke-Davies as 20 mg tablets. Ground tablets were added to ground mouse chow to a final concentration of 1500 mg atorvastatin/kg ground chow. Assuming a daily food intake of 2–3 g of 25 g mice this should correspond to a daily dose of 120–180 mg/kg.

The total hepatic cholesterol was determined, following extraction and subsequent drying under nitrogen from liver samples, as described (Rudling M. J. Lipid Res. 33: 493–50 1992). Total hepatic and plasma cholesterol and plasma triglycerides were assayed using commercial available methods (Boehringer-Mannheim, Mannheim, Germany).
Enzymatic Activities of HMG CoA Reductase and C7αOH Hepatic microsomes were prepared by differential ultra-centrifugation of liver homogenates in the absence of fluoride as previously described (Angelin et al 1984, J Lipid Res. 25; 1159–1166, Einarsson et al. 1986, J. Lipid Res. 27; 82–88, Einarsson et al. 1989, J. Lipid Res. 30; 739–746). Microsomal HMG CoA reductase was assayed from the conversion of [$^{14}$C] HMG CoA to mevalonate, and expressed as picomoles formed per mg protein per min. The activity of C7αOH was determined from the formation of 7α-hydroxycholesterol (picomoles/mg protein/min) from endogenous microsomal cholesterol by the use of isotope dilution-mass spectrometry as described in detail. All enzyme assays were carried out in duplicate.

Ligand blot assay of LDL-receptors was performed using $^{125}$I-labeled rabbit β-migrating very low density lipoprotein (VLDL), as described previously (Rudling et al 1992. PNAS 89; 6983–6987). Membrane proteins were separated by SDS-PAGE (6% poly-acrylamide). After electrotransfer of proteins to nitrocellulose filters and subsequent incubation $^{125}$I-β-VLDL filters were exposed onto DuPont X-ray film at −70° C.
Size-fractionation of Lipoproteins by Fast Performance Liquid Chromatography (FPLC)

Equal volumes of plasma from each animal were pooled (1–2 mL) and the density was adjusted to 1.21 g/mL with solid KBr. After ultracentrifugation at $10^5$ g for 48 h, the supernatant was removed and adjusted with 0.15 M NaCl, 0.01% etylene diamine tetraacetic acid, (EDTA), 0.02% sodium azide, pH 7.3. An aliquot of this solution was injected on a 54×1.8 cm superose 6B column after filtration through a Millipore 0.45 mm HA filter, 2-mL fractions were collected.
Fecal Bile Acid Excretion This was measured by the method of Beher, W. T. S. et al. 1981 Steroids. 38: 281–295 as modified by Wolle et al. 1995, J.Clin. Invest. 96: 260–272. Briefly, feces were collected twice for two consecutive days and homogenized in two volumes (v/w) of water. Aliquots (corresponding to 1 g of feces) were incubated for 30 min. at 70° C., after addition of 7 mL of ethanol. The mixture was filtered through a paper filter that was then rinsed once with 6 mL of 70° C. ethanol. After drying a 4 mL aliquot under nitrogen, 2 mL of 3M NaOH were added and samples were hydrolyzed by incubation at 100° C. for 2 h. After adjusting pH to 9, the bile acid concentration was measured in a 70 μL aliquot using a fluorescence system based on resazurin.

EXAMPLE 1
Effects of GH on Plasma Lipids and Hepatic Cholesterol Metabolism

Infusion of GH to C57BL/6J and LDLRKO mice. Two sets of ten animals of each strain were continuously infused at a rate of 1 mg/kg/d. After six days of treatment, animals were killed and plasma and livers were collected.

Total plasma cholesterol and triglycerides were increased by 250 and 80%, respectively in LDLRKO animals as compared to C57BL/6J mice (FIG. 1). There was also a 45% increase of total hepatic cholesterol in LDLRKO animals. Treatment with GH clearly reduced the total plasma cholesterol in LDLRKO animals whereas no significant effect was obtained in C57BL/6J mice. GH infusion to normal mice slightly increased total hepatic cholesterol whereas there was a slight reduction in LDLRKO animals. There was a slight but not significant reduction of total plasma triglycerides in LDLRKO animals whereas total plasma triglycerides were unaltered in C57BL/6J mice.

FPLC separation of plasma lipoproteins showed that the reduction of cholesterol induced by GH in LDLRKO animals was within all size fractions (FIG. 2), although most pronounced within VLDL and LDL particles; the reduction in triglycerides was only within VLDL particles (FIG. 3). In C57BL/6J mice GH increased triglycerides within VLDL particles.

The absence of LDL receptors in LDLRKO animals was confirmed by ligand blot of hepatic membranes obtained from pooled livers from each animal group, using β-VLDL as ligand (not shown). The expression of LDL receptors in C57BL/6J mice was not altered by GH treatment.

To confirm this surprising finding of a plasma cholesterol lowering effect of GH in LDLR deficient animals with pronounced hypercholesterolemia, the previous experiment was repeated. In addition, we wanted to also determine the enzymatic activities of 3-hydroxy-3-methyl-glutaryl coenzyme A, (HMG CoA) reductase, and cholesterol 7α hydroxylase, (C7αOH), being the rate limiting steps in the synthesis of cholesterol and bile acids, respectively. Animals received the same dose of GH that was infused for six days. Subsequent assay of total plasma cholesterol and triglycerides, and total hepatic cholesterol (FIG. 4) showed practically identical results, although the reduction of total plasma cholesterol was slightly less pronounced.

FPLC separation of plasma lipoproteins confirmed that GH lowered plasma lipoprotein cholesterol, particularly within VLDL and LDL particles (FIG. 5). In this experiment triglycerides were not only reduced among VLDL particles but also within LDL and HDL particles (FIG. 6).

Assay of C7αOH activity showed a 40% increase in LDLRKO animals as compared to C57/BL6J animals (FIG. 7). Treatment with GH clearly increased the activity in both animal groups (by 115 and 46% for C57BL/6J and LDL-RKO mice, respectively). The enzymatic activity of HMG CoA reductase was strongly suppressed in LDLRKO animals (30% of that found in control C57/BL6J animals, FIG. 8). GH treatment increased the activity of HMG CoA reductase in C57/BL6J and LDLRKO mice, by 53 and 113%, respectively. Assay of the mRNA levels for C7αOH by solution hybridization, (FIG. 9) showed a 60% reduced abundance in LDLRKO animals, as compared to C57/BL6J animals. GH treatment increased the C7αOH mRNA level by 170% in LDLRKO mice, whereas there was a 50% reduction in the C7αOH mRNA level in C57/BL6J animals following GH treatment.

HMG CoA reductase mRNA levels were slightly reduced in LDLRKO animals compared to C57BL/6J animals and GH infusion increased these by 20% whereas there was no effect in C57/BL6J mice.

Thus, as in normal rats (P. Parini, et al. 1998. Cholesterol and lipoprotein metabolism in aging: reversal of hypercholesterolemia by growth hormone treatment in old rats. Arterioscl. Thromb. & Vasc. Biol. In press), there was no reduction of plasma cholesterol in normal mice following treatment with GH, which also is in line with previous results on Sprague Dawley rats (Rudling et al, 1997, J. Clin. Invest. 99; 2239–2245). GH treatment of mice also stimulated the activity of C7αOH, both in normal and LRLRKO animals. However, the activity of HMG CoA reductase was strongly suppressed in LDLRKO animals, and GH infusion increased the activity to the same level as found in normal C57BL/6J animals. This latter effect should theoretically strongly counteract the plasma cholesterol lowering effect of the hormone.

EXAMPLE 2

GH Treatment Potentiates the Effects of Bile Acid Sequestrants and HMG CoA Reductase Inhibitors on Plasma Lipids To evaluate if GH treatment could have beneficial effects in combination therapy with established lipid lowering drugs such as statins and bile acid sequestrants, groups of 5 mice were treated with cholestyramine, atorvastatin and GH alone and in combination. After 6 days of treatment, animals were bled from the eye and assayed for cholesterol and triglycerides.

At the doses employed there were no effects on cholesterol following treatment with atorvastatin or cholestyramine alone whereas there was a 10% reduction following GH. Atorvastatin and GH both reduced plasma triglycerides by approx. 20%. When GH was given in combination with cholestyramine or atorvastatin plasma cholesterol was reduced by 29 and 36% respectively, and triglycerides were reduced by 34 and 43%, respectively. Combination of all three drugs resulted in the strongest effect on plasma cholesterol, and a 43% reduction was obtained. Triglycerides were not further reduced.

Assay of the content of fecal bile acids prior to and during treatment with the three drugs revealed that all three drugs could increase fecal bile acids when given alone (FIG. 11). Fecal bile acids were highest when GH was combined with cholestyramine, whereas no further change was obtained when GH was combined with atorvastatin or with cholestyramine.

Figure 1:
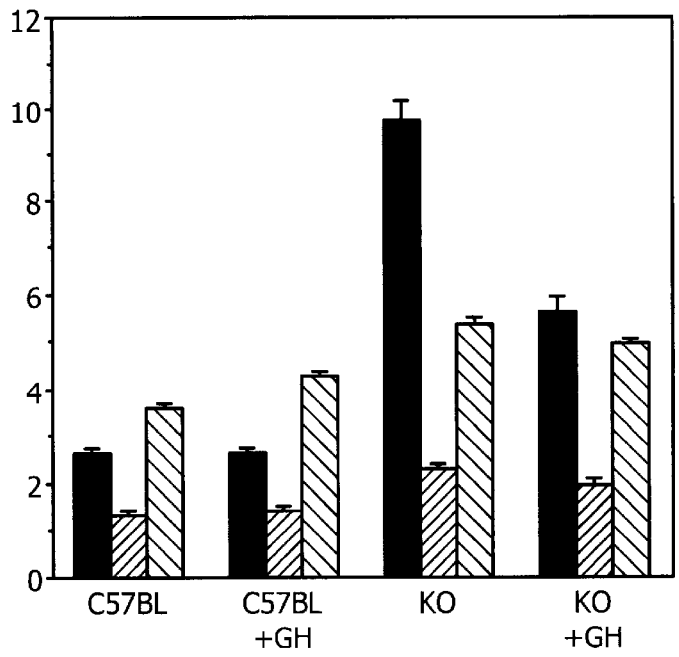
FIG. 1 is a graph that depicts total plasma cholesterol, triglycerides and total hepatic cholesterol in normal (C57 BL) and LDLRKO (KO) mice±GH (1 mg/kg/day) for 6 days. Each group consisted of 10 animals. Bars indicate SEM.
Figure 2:
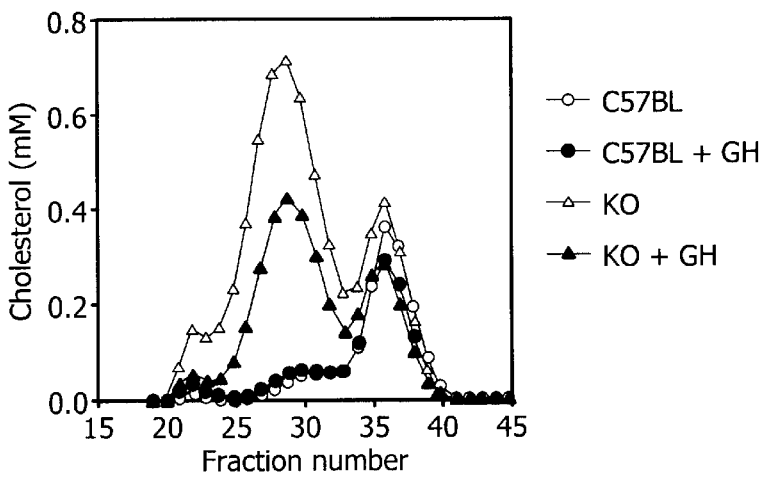
FIGS. 2 and 3 show the lipoprotein patterns in the four groups of animals described in legend to FIG. 1. Equal volumes of plasma from each animal were pooled and subjected to ultracentrifugation at density 1.21. The supernatant was thereafter separated on a Superose 6 column and fractionated. Total cholesterol and total triglycerides were finally determined and the results are presented in FIGS. 2 and 3, respectively.
Figure 3:
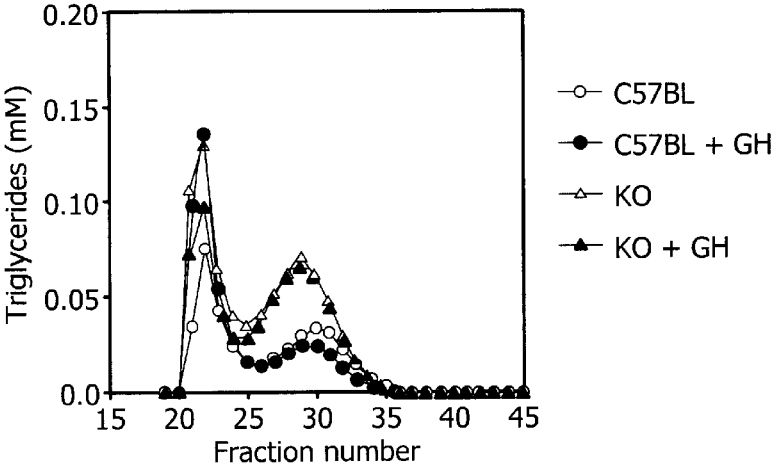
Figure 4:
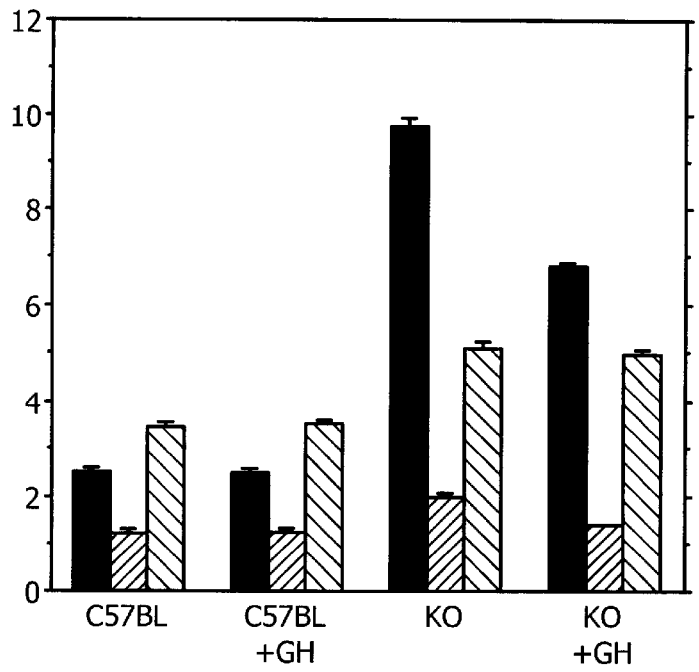
FIG. 4 shows total plasma cholesterol, triglycerides and total hepatic cholesterol in normal C57 BL and LDLRKO (KO) mice±GH (1 mg/kg/day) for 6 days in a repeated experiment. Each group consisted of 10 animals. Bars indicate SEM.
Figure 5:
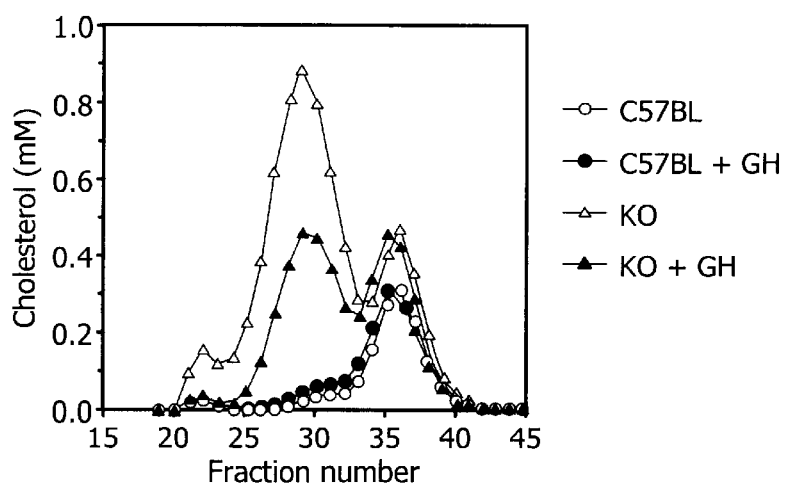
FIGS. 5 and 6 demonstrate the lipoprotein patterns (cholesterol and triglycerides) in the four groups of animals described in legend to FIG. 4 after separation of pooled plasma by FPLC.
Figure 6:
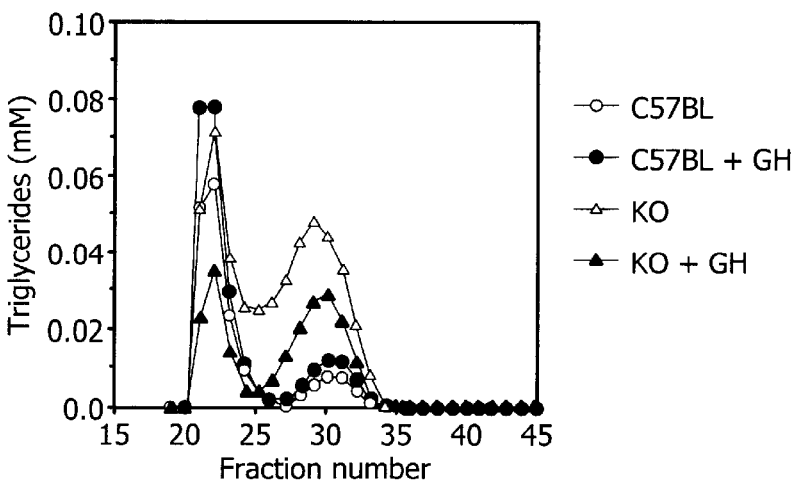
Figure 7:
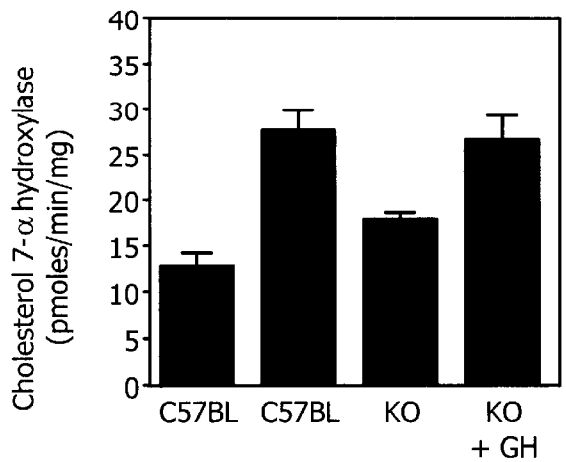
FIG. 7 shows the enzymatic activity of C7αOH in microsomes prepared from pooled liver samples of the four groups of animals described in legend to FIG. 4. The means and standard error of means from three separate pools of all animals are shown.
Figure 8:
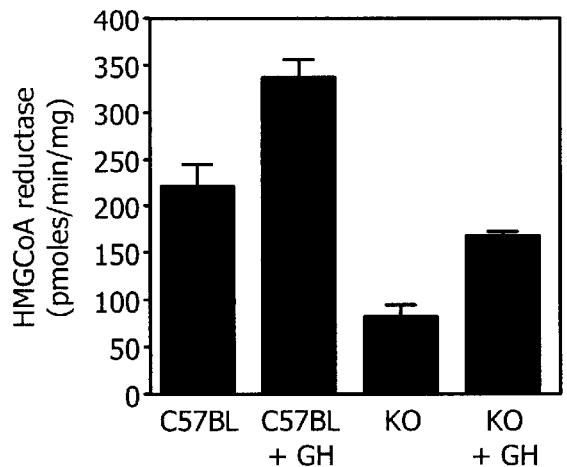
FIG. 8 shows the enzymatic activity of HMG CoA reductase in microsomes prepared from pooled liver samples of the four groups of animals described in legend to FIG. 4. The means and standard error of means from three separate pools of all animals are shown.
Figure 9:
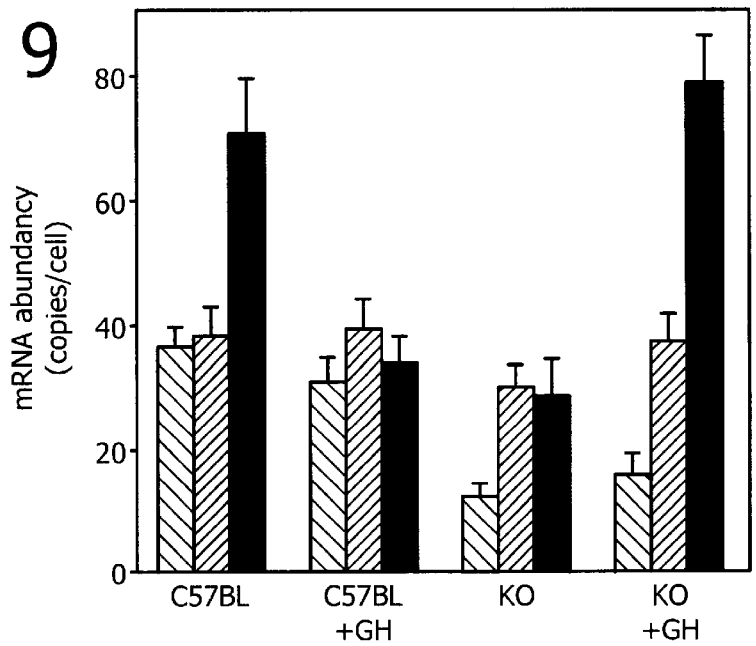
FIG. 9 shows the mRNA abundance for the LDLR, HMG CoA reductase and C7αOH determined by solution hybridization. Total nucleic acids were extracted from a sample of liver from each individual and incubated with the respective complementary radio-labeled cRNA probe.
Figure 10:
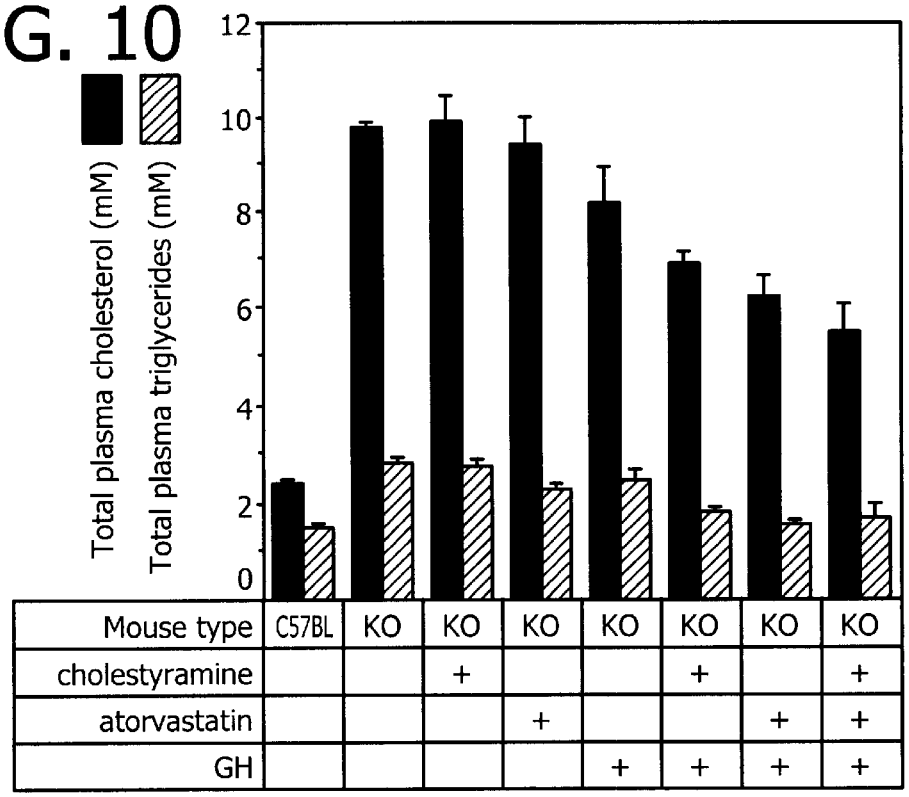
FIGS. 10 and 11 show the total plasma cholesterol and triglyceride levels and the fecal bile acid content in LDL-RKO mice following 6 days of treatment with cholestyramine, atorvastatin and GH. The three drugs were given alone or in the indicated combinations to groups of 5 mice at doses described below under methods; Animals and experimental procedure. After 6 days of treatment animals were bled from the eye under light ether anesthesia for the determination of total cholesterol and triglycerides, (FIG. 10). Feces was collected during two days at two occasions; the first occasion starting 4 days prior to initiation of treatment (FIG. 11, open bars) and from day 3 to day 5 during drug treatment (FIG. 11, filled bars).
Figure 11:
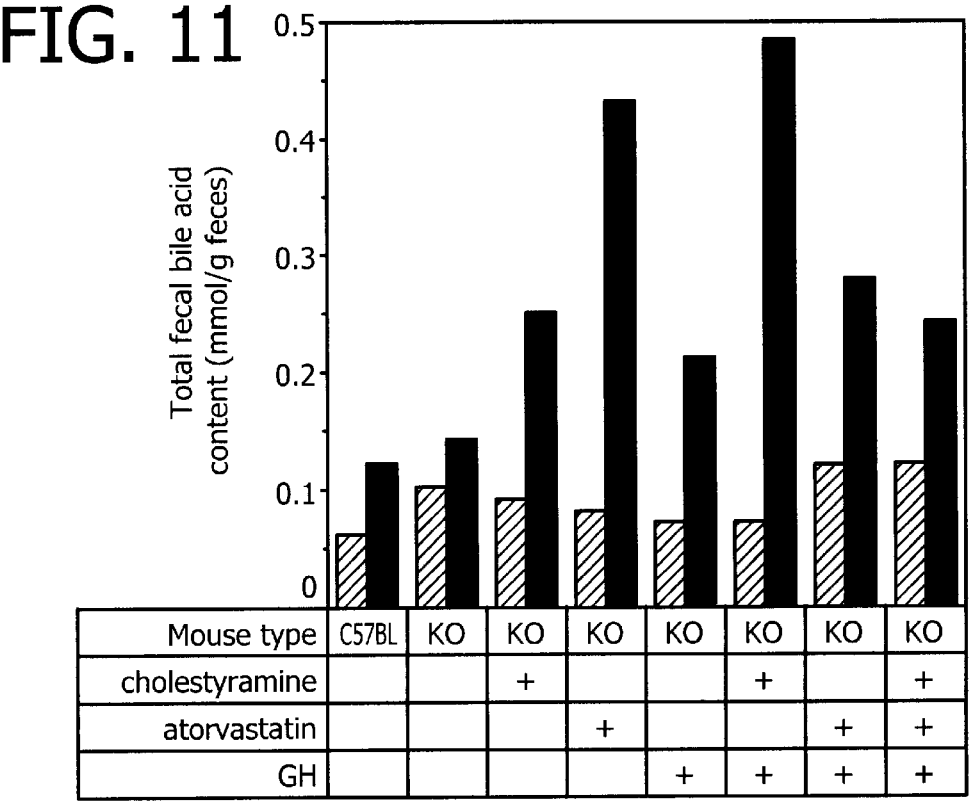

What is claimed is:

1. A method for the treatment of a mammal with familial hypercholesterolemia of homozygous form comprising administering to said mammal a therapeutically effective amount of growth hormone or a prevalent amount of a growth hormone releasing compound selected from the group growth-hormone releasing hormone, somatostatin-antagonists, hexarelin and Merck growth hormone releasing compound L-692 429, wherein the administered amount is effective to treat a mammal with familial hypercholesterolemia.

2. A method for the treatment of a mammal with familial hypercholesterolemia of homozygous form comprising administering a compound as disclosed in claim 1 in combination with a lipid-lowering agent selected from the group consisting of 3-hydroxy-3-methyl-glutaryl coenzyme A reductase inhibitors and bile acid sequestrants.

3. A method for the treatment of a mammal with familial hypercholesterolemia of homozygous form according to claim 2 comprising the administering of growth hormone and cholestyramine.

4. A method for the treatment of a mammal with familial hypercholesterolemia of homozygous form according to claim 2 comprising the administering of growth hormone and statins.

5. A method for the treatment of a mammal with familial hypercholesterolemia of homozygous form according to claim 4 comprising the administering of growth hormone and atorvastatin.

6. A method for the treatment of a mammal with familial hypercholesterolemia of homozygous form according to claim 2 comprising the administering of growth hormone, cholestyramine and atorvastatin.

7. A method for the treatment of a mammal with familial hypercholesterolemia of homozygous form according to claim 1 comprising the administering of growth hormone in natural or recombinant form.

8. A method for the treatment of a mammal with familial hypercholesterolemia of homozygous form according to claim 1 comprising the administering of from 0.02 to 0.14 IU per kilo body weight per day of growth hormone.

* * * * *